United States Patent [19]

Zanardelli

[11] Patent Number: 4,652,745

[45] Date of Patent: Mar. 24, 1987

[54] OPTICAL MOISTURE SENSOR FOR A WINDOW OR WINDSHIELD

[75] Inventor: Vance P. Zanardelli, Birmingham, Mich.

[73] Assignee: Ford Motor Company, Dearborn, Mich.

[21] Appl. No.: 805,528

[22] Filed: Dec. 6, 1985

[51] Int. Cl.[4] ........................................... G01N 21/17
[52] U.S. Cl. ................................. 250/227; 250/577; 340/602
[58] Field of Search ................ 250/227, 577; 73/73, 73/293; 340/602; 356/135–137

[56] References Cited

U.S. PATENT DOCUMENTS

| | | |
|---|---|---|
| 2,977,842 | 4/1961 | Duke . |
| 3,540,025 | 10/1970 | Levin et al. . |
| 3,639,770 | 2/1972 | Zizelmann . |
| 3,917,411 | 11/1975 | Schweizer et al. . |
| 4,221,962 | 9/1980 | Black et al. ........................ 250/227 |
| 4,427,879 | 1/1984 | Becher et al. . |

FOREIGN PATENT DOCUMENTS

| | | |
|---|---|---|
| 2420594 | 11/1975 | Fed. Rep. of Germany . |
| 0084141 | 5/1984 | Japan .................................. 340/602 |
| 0085944 | 5/1984 | Japan .................................. 340/602 |
| 1242621 | 8/1971 | United Kingdom . |

*Primary Examiner*—Edward P. Westin
*Attorney, Agent, or Firm*—Peter Abolins; Keith L. Zerschling

[57] ABSTRACT

A windshield moisture detector has two identical, symmetrically positioned prisms with an elongated body between an integral reflector and light transducer cavity. One light transducer cavity contains a light source and the other a light detector. The reflectors are angled so that when the moisture detector is partially in contact with the windshield, light can travel between the two reflectors through a light path in the window. The magnitude of light transmitted through the windshield is indicative of moisture on the windshield.

12 Claims, 14 Drawing Figures

DRY
TOTAL REFLECTION

WET
PARTIAL REFLECTION

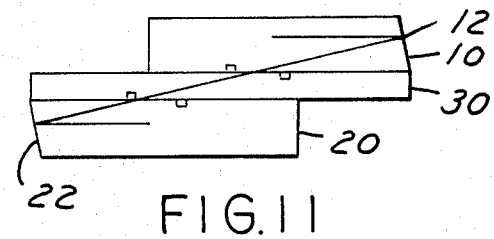
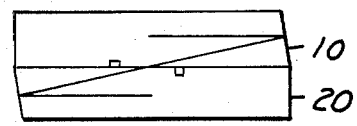
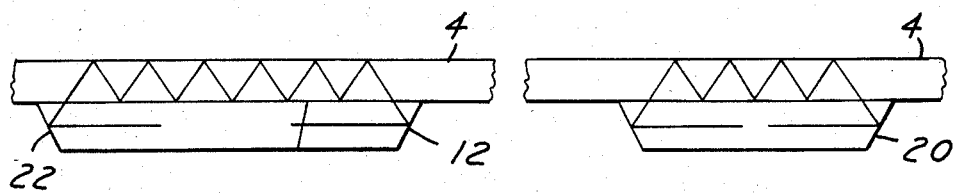
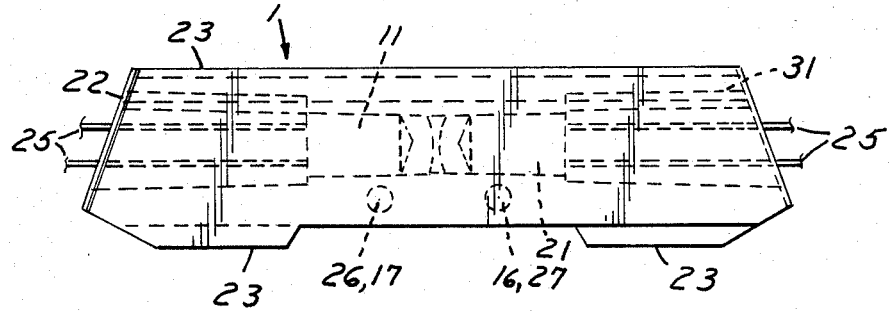
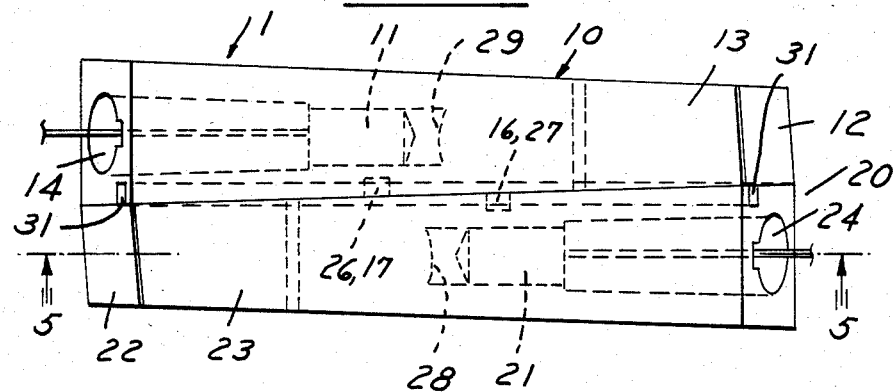

OPTICAL MOISTURE SENSOR FOR A WINDOW OR WINDSHIELD

BACKGROUND OF THE INVENTION

1. Field of the Invention

This invention relates to the structure of a device for sensing moisture on a window using reflection of a light beam.

2. Prior Art

British Pat. No. 1,242,621 and German Pat. No. (Offenlegungsschrift 24 20 594) both disclose an optical sensor for detecting rain on an automobile's windshield. Both sensors operate on the principal of the reflection of light. That is, a pair of prisms are secured to an inner surface of the window and project a beam of light through one prism to the other prism using a path which extends in the interior of the window. One of the prisms detects light emerging from the window so that the intensity of light detected by the detecting prism is decreased in the presence of condensation on the outside of the window.

In operation, when a light beam enters a sheet of transparent material at such an angle that it is totally reflected at one of the inside surfaces, the beam will continue to travel to and fro inside the sheet until it can be refracted to the outside through another object contacting the transparent material of the sheet. The light source provides a beam of light which is projected into the window material at an angle so that the light is totally reflected at the other surface of the window and then back again to the entry surface and thus to and fro until it leaves the interior of the window through the second prism and impinges upon a photodetector. This will be the case for as long as the surface of the window is actually dry. However, as soon as the outside surface of the window has some water droplets thereon, the light beam traveling through the interior of the window is transmitted outwardly through the external surface and into the droplets. The beam is thus prevented from reaching the photodetector or at least the intensity of the reflected part of the beam is reduced. This causes the photodetector to operate an output signal which is used to indicate the presence of water or actuate a windshield wiper.

However, neither of these patents teach a simple, readily manufacturable, compact plastic package for the entire moisture sensor unit including light sources, lenses, light reflectors and light detectors.

U.S. Pat. No. 3,639,770 to Zizelmann teaches an optical sensor incorporating a light source and a light receiver and a light permeable mass of resin material. For the disclosed sensor device to function as a detector of moisture on a windshield, the device would have to be mounted on the outside of the windshield. This is undesirable because it exposes the sensor to the environment, hinders cleaning of the windshield, and prevent placement of the sensor in the wipe path.

U.S. Pat. No. 4,427,879 to Becher et al teaches an optical connector assembly having mating parts, each of which has a cavity for receiving a photoelectric device. The invention relates to optoelectronic connector assembly systems including electrical connector parts for housing optoelectronic transducers and to optical connector parts for housing terminal portions of a fiber optic light guide. A fiber optic light guide has an integral lens associated therewith. Formation of the lens is taught through the application of heat to the end of the optical fiber. Surface tension effects dictate the shape of the lens and do not teach a spherical shape internal to a device such as a moisture detector. Thus, even though there is a general teaching of forming a lens there is no teaching of an advantageous moisture detector structure for use in conjunction with the inside of a windshield.

Also, generally related to the transmission or detection of light are U.S. Pat. No. 2,977,842 issued to Duke, U.S. Pat. No. 3,540,025 issued to Levin et al, U.S. Pat. No. 3,917,411 issued to Schweizer and U.S. Pat. No. 4,221,962 issued to Black. Again, none of these patents teach or suggest a simple readily manufacturable compact plastic package for the entire moisture sensor unit.

It would be desirable to be able to form such a simple moisture detector which is readily manufacturable and can be easily mounted on the inside of a windshield. Further, it is desirable that such a detector be unaffected by the ambient light intensity. None of the above patents addresses this ambient light problem. For example, the above-cited British and German patents, in the configurations presented, allow ambient light a direct path into the light receiving element. Since ambient light will often be significantly greater in intensity than the self-contained light source, some sort of compensation would have to be employed so that the output of the moisture detector would be a true indication of moisture. These are some of the problems this invention overcomes.

SUMMARY OF THE INVENTION

This invention teaches a moisture detector, using two identical prisms, for a window. Each prism can be simply manufactured by molding and then can be joined to another such prism to form the moisture detector with symmetrical positioning of the prisms. Each prism includes a main elongated light conducting body having a longitudinal axis with a light transducer cavity at one end and an integral reflector at the other end. In the moisture detector, one of the light transducer cavities contains the light source and the other contains a light detector. The two prisms are positioned next to each other so that the reflectors are at opposite ends. The reflector of each prism is angled so that a component of reflected light in a first plane, defined by the two longitudinal axes of the prisms, is pointed toward the reflector of the other prism. Further, a component of reflected light in a second plane, perpendicular to the first plane and including a line of sight between the two reflectors, is pointed toward the window so that the amount of internal reflection within the window is affected by the presence of moisture on the other side of the window from the moisture detector.

Advantageously, each of the prisms has a flat contact surface adjacent the reflector for passing light between the prism and the window. Further, advantageously, the rest of the prism is covered with a nonlight transmitting material.

A structure in accordance with an embodiment of this invention is relatively unaffected by ambient light intensity. The ambient light cannot enter the prism at an angle of greater magnitude than the critical angle for the air glass interface, about 41°, and must therefore reflect off the bottom surface of the prism before reaching the light detector element. The bottom surface has a very low reflectivity, such as flat black, so that the ambient light intensity at the receiver will be negligible.

Thus, such a device is relatively immune to the effects of ambient light levels.

The identical configuration of the two prisms provides for easy manufacturability and increased installation flexibility. For example, one sensor design can be used for installations having different glass thicknesses and sensing surface areas. This is accomplished by using a spacer or shim, between the two identical prism members. The shim can have coupling means to each of the prisms so that the two prisms can be mounted longitudinally and transversely displaced from one another, still maintaining symmetrical positioning with respect to each other. This can be done to compensate for a thicker glass cross section or to increase the sensing area by increasing the light path between the two reflectors so that there are more internal reflections within the window between the location of the two prism reflectors.

An embodiment in accordance with this invention provides a compact package relative to the sensing surface area. Alignment tolerance stackup problems are eliminated by an integral design. That is, there is no need to individually locate and fix a prism, a mirror, a lens or electroptic component. The embodiment has relatively low material and fabrication costs.

BRIEF DESCRIPTION OF THE DRAWINGS

FIG. 9 is a plan schematic view showing a light path of two coupled prisms with an intermediate shim to space the two prisms laterally and longitudinally so as to increase the light path in accordance with an embodiment of this invention;

FIG. 10 is a plan schematic view of two symmetric prisms joined to each other and a representation of a light path between two reflectors in accordance with an embodiment of this invention;

FIG. 11 is a schematic side view of the prism of FIG. 9 and the light path in an adjacent window in accordance with an embodiment of this invention;

FIG. 12 is a schematic side view of the prism of FIG. 10 and the light path in an adjacent window in accordance with an embodiment of this invention;

FIG. 13 is a side view of a moisture detector with two joined prisms and the internal components in dotted outline in accordance with an embodiment of this invention; and FIG. 14 is a plan view of the moisture sensor of FIG. 13 with two adjacent identical prisms and the internal light transducer cavities and reflectors shown in dotted outline.

DETAILED DESCRIPTION OF THE INVENTION

Figure 1:
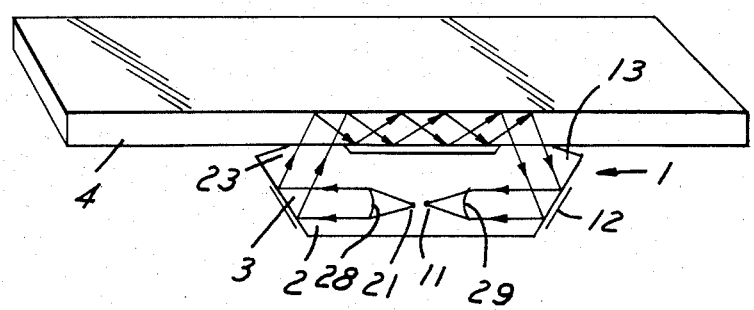
FIG. 1 is a perspective schematic view of a window and a moisture detector showing the light path in accordance with an embodiment of this invention.
Figure 2:
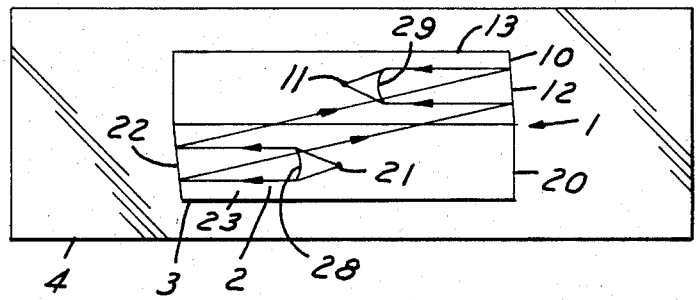
FIG. 2 is a plan view of the moisture sensor and window assembly with light paths of FIG. 1.

Referring to FIGS. 1 and 2, a moisture sensor 1 includes a prism 10 and a coupled adjacent identical prism 20. Prism 20 includes a light source 21 and prism 10 includes a light receiver 11. Light paths 2 and 3 travel from light source 21 through lens 28 to a reflector 22 in the end of prism 20, out of prism 20 through a contact pad 23 into a window 4. Light paths 2 and 3 then are internally reflected within window 4 until a contact pad 13 in prism 10. Light paths 2 and 3 then strike a reflector 12 of prism 10, pass through lens 29, and are detected by light detector 11.

Figure 3:
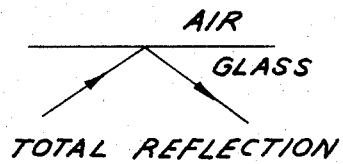
FIG. 3 is a schematic drawing of total light reflection at a glass-air interface.
Figure 4:
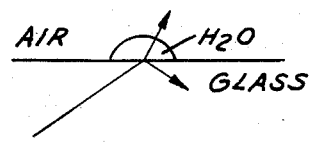
FIG. 4 is a schematic diagram showing the partial reflection at a glass-air interface with water on the glass.

As can be seen from FIGS. 3 and 4, the amount of light entering contact pad 13 with respect to the amount of light leaving contact pad 23 is a function of the amount of total internal reflection within window 4. That is, if there is water on the glass, some of the light is refracted out of the window as shown in FIG. 4. Further, contact pad 13 is positioned so that ambient light does not have a direct, unreflected light path to light detector 11.

As a result, sensor 1 detects the presence of water on the surface of windshield 4. Moisture sensor 1 transmits a collimated light beam into the glass of windshield 4 at an angle, measured normal to the surface, greater than the critical angle of a glass to air interface. Hence, total internal reflection occurs at the surfaces of the glass. The beam of light is then intercepted at the surface and transmitted out of the glass back into sensor 1. The entrance and exit of light at greater than the critical angle is possible because the sensor is optically bonded to the glass at the entrance and exit points. Therefore, the light reaches a continuous medium between windshield 4 and sensor 1 and not a surface interface. Since the critical angle of any interface is dependent upon the relative indices of refraction of the two mediums, changing one of the mediums will affect the angle at which total reflection occurs. Therefore, when water strikes the surface of the glass, thereby replacing air with water as the second medium, the critical angle changes. Since water has a higher index of refraction than air, the angle is decreased. A portion of the light is then refracted out of the glass, reducing the amount of light reaching the receiver.

A construction of moisture sensor 1 includes two identical prisms 20 and 12, positioned symmetrically. Advantageously, the prisms are injection molded, vacuum metallized and painted acrylic components. A typical fabrication for the two prisms that comprise a moisture detector includes injection molding both prisms using clear acrylic, cleaning the components, vacuum metallizing the reflector surface of each part, masking the contact pad of each part and spray painting the parts flat black, inserting a light source such as light emitting diode in one prism and a light detector such as a photodiode in another prism, joining the two parts together by rotating one part 180° so as to align coupling pins and openings and pressing the two prisms together. The moisture sensor is then bonded to the windshield using an optically clear cement on the two upraised contact pads.

Figure 5:
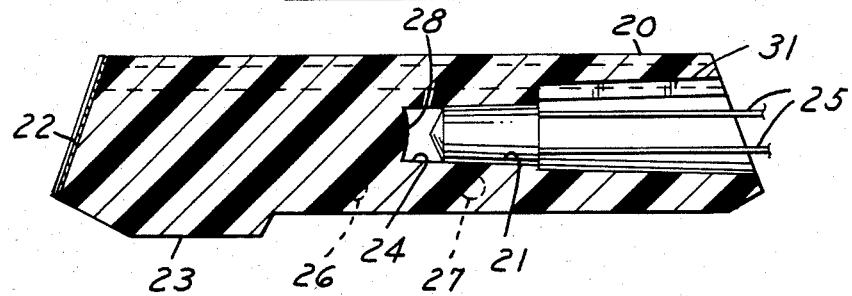
FIG. 5 is a cross section view of a prism in accordance with an embodiment of this invention.

Referring to FIG. 5, a cross section of a prism 20 shows light source 21 as being a light-emitting diode mounted in a light transducer cavity 24 with integral lens 28. Wires 25 extend out of the rear opening of cavity 24 from light-emitting diode 21. The wires may then be routed through slot 31 if desired. Reflector 22 is a metallized portion on the end of prism 20. Contact pad 23 is a portion of the surface of prism 20. Advantageously, the remainder of the surface of prism 20 adjacent pad 23 is spaced from window 4 so as not to interfere with internal reflections within window 4.

Figure 6:
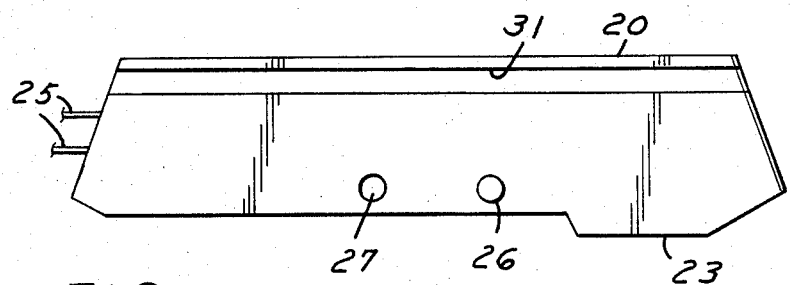
FIG. 6 is a side elevation view of a prism in accordance with an embodiment of this invention showing a projection and indentation for coupling two identical prisms.
Figure 7:
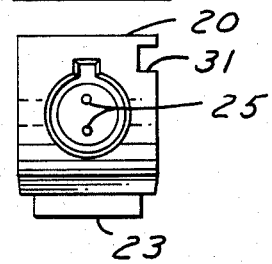
FIG. 7 is an end view of a prism showing an opening of a light transducer cavity in accordance with an embodiment of this invention.
Figure 8:
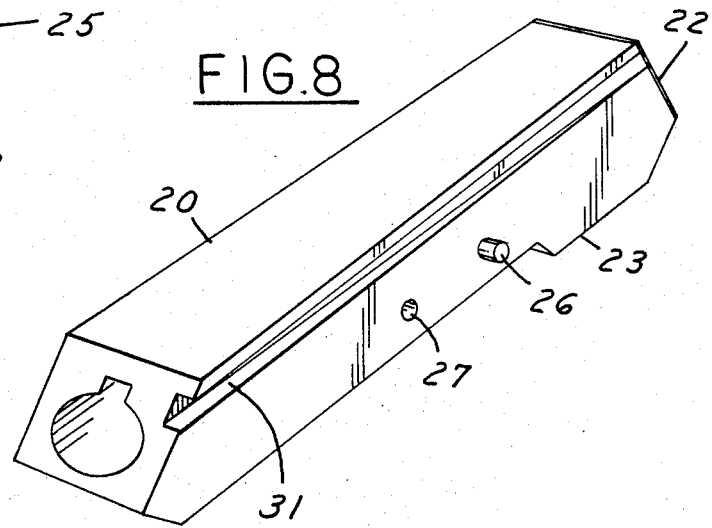
FIG. 8 is a perspective view of a prism showing the opening of a light transducer cavity and a coupling projection and indentation in accordance with an embodiment of this invention.

Referring to FIGS. 8 and 6, a cylindrical projection 26 extends out from the side of prism 20 and an indentation 27 is formed into the side of prism 20 for receiving a projection from identical symmetrically positioned prism 10. Prism 10 is identical to prism 20 and is similarly numbered with the exception that instead of a light source 21, prism 10 has a light detector 11, such as a photodiode.

Referring to FIG. 9, prisms 10 and 20 can be transversely and longitudinally displaced from one another by a shim 30. As a result, as seen in FIG. 11 there is a longer light path between reflectors 12 and 22. Shim 30 can have a projection and an indentation on each side to receive the indentations and projections of prisms 10 and 20. The thickness of shim 30 and the longitudinal displacement of the projections and indentations on opposing sides of shim 30 are such that the light path between reflectors 22 and 12 is on a line of sight between reflectors 22 and 12. The longer light path is advantageous to accommodate different thicknesses of glass and to provide an increased sensing area.

Referring to FIGS. 10 and 12, prisms 10 and 20 are joined to one another without the use of a shim 30 and have a configuration as shown in FIGS. 1 and 2.

Referring to FIGS. 13 and 14, a moisture sensor 1 is shown as being a combination of identical, symmetrically positioned prisms 10 and 20. A cross section 5—5 of prism 20 in FIG. 14 is shown as FIG. 5.

The section line 5—5 of FIG. 14 is along the longitudinal axis of prism 20. Similarly, prism 10 has longitudinal axis parallel to longitudinal axis of prism 20 when joined together and a first plane is defined by the two parallel axes. The relative orientation of the angle of each of the reflectors with respect to the longitudinal axis, i.e., of reflector 22 with respect to the longitudinal axis of prism 20 and reflector 12 with respect to the longitudinal axis of prism 10, must be such that a component of the reflected light is aimed at the opposing symmetric reflector. Also, the light must be reflected at an angle, in a second plane perpendicular to the first plane and along the line of sight between the two reflectors, sufficiently toward the window such that the source light exits contact pad 23 and that the source light can enter contact pad 13 and then hit reflector 12.

In summary, the reflector of each prism is angled so that a component of reflected light in the first plane defined by the two longitudinal axes is pointed toward the reflector of the other prism and that a component of reflected light in the second plane, perpendicular to the first plane and including a line of sight between the two reflectors is pointed toward the window so that the amount of internal reflection within the window is affected by the presence of moisture on the other side of the window from the moisture detector.

Both of the prisms 10, 20 have respective integral lenses 29, 28 adjacent the light transducer cavities. Advantageously, lenses 29 and 28 are spherical and provide a focusing of parallel light rays to radial rays converging on a focal point and vice versa.

Various modifications and variations will no doubt occur to those skilled in the arts to which this invention pertains. For example, the particular coupling means between the two prisms can be varied from that disclosed herein. These and all other variations which basically rely on the teachings through which this disclosure has advanced the art are properly considered within the scope of this invention.

I claim:

1. A moisture detector for a window comprising two substantially identical prisms, positioned substantially symmetrically, each prism including:
    a main elongated, light conducting body having a longitudinal axis, a light transducer cavity at a first end and an integral reflector at a second end, opposite from said first end, so that light can travel along a light path between said light transducer cavity and said reflector;
    said two prisms being positioned adjacent to each other so the longitudinal axes of each are parallel and the reflector end of a first prism is adjacent to the light transducer cavity of a second prism and vice versa, and being positioned so that the window adjacent to said two prisms is substantially parallel to a plane defined by the two longitudinal axes of said two prisms; and
    said reflector of each prism being angled so that a component of reflected light in a first plane defined by the two longitudinal axes is pointed toward the reflector of the other prism and that a component of reflected light in a second plane, perpendicular to said first plane and including a line of sight between the two reflectors is pointed toward the window so that the amount of internal reflection within the window is affected by the presence of moisture on the other side of the window from said moisture detector.

2. A moisture detector as recited in claim 1 further comprising an integral lens incorporated in each prism, at one end of said light transducer cavity, for transforming between parallel light rays and radial light rays.

3. A moisture detector as recited in claim 2 further comprising:
    a light source positioned in said light transducer casing of said first prism; and
    a light receiver positioned in said light transducer cavity of said second prism.

4. A moisture detector as recited in claim 3 wherein each of said light conducting bodies has a flat contact area adjacent the second end for abutting the window and a portion spaced from the window on the side of the light conducting body facing the window so as to provide increased light path coupling between the window and said prisms adjacent said reflectors and reduced light path coupling between the window and said prisms at other locations, and
    said flat contact area being positioned so that ambient light does not have a direct, unreflected light path to a light transducer cavity.

5. A moisture detector as recited in claim 4 further comprising a coupling means between said two prisms.

6. A moisture detector as recited in claim 5 wherein said coupling means on each of said prisms is a projection and an indentation adapted to mate with an identical indentation and projection, respectively, on the other prism.

7. A moisture detector as recited in claim 6 wherein said moisture detector is coated with a nonlight transmitting material, except for each of said contact areas adjacent each of said reflectors.

8. A moisture detector as recited in claim 7 wherein said light transducer casing is generally cylindrical.

9. A moisture detector as recited in claim 7 wherein the interface between said first prism and said second prism is along a plane at an angle to the longitudinal axes of said first and second prisms.

10. A moisture detector as recited in claim 7 wherein each of said prisms is formed of injection molded transparent acrylic.

11. A moisture detector as recited in claim 1 wherein said two prisms are longitudinally offset with respect to one another.

12. A moisture detector as recited in claim 1 further comprising an intermediate shim for laterally and longitudinally spacing the two prisms so as to provide an increased light path between the two reflectors, said shim including symmetric coupling means on opposing sides of the shim for coupling to each of the prisms, the width of the shim and longitudinal displacement of the coupling means being such that light can be reflected with components in a direction along the line of sight between the two reflectors.

* * * * *